United States Patent [19]

Chen

[11] 4,369,284
[45] Jan. 18, 1983

[54] THERMOPLASTIC ELASTOMER GELATINOUS COMPOSITIONS

[75] Inventor: John Y. Chen, Pacifica, Calif.

[73] Assignee: Applied Elastomerics, Incorporated, Pacifica, Calif.

[21] Appl. No.: 134,977

[22] Filed: Mar. 28, 1980

Related U.S. Application Data

[63] Continuation-in-part of Ser. No. 916,731, Jun. 19, 1978, abandoned, which is a continuation-in-part of Ser. No. 815,315, Jul. 13, 1977, abandoned, which is a continuation-in-part of Ser. No. 778,343, Mar. 17, 1977, abandoned.

[51] Int. Cl.$^3$ .............................................. C08K 5/01
[52] U.S. Cl. .................................. 524/476; 524/490; 524/505; 525/95
[58] Field of Search ................. 260/33.6 R, 33.6 VA, 260/33.6 AQ; 525/95; 524/476, 490, 495

[56] References Cited

U.S. PATENT DOCUMENTS

| | | | |
|---|---|---|---|
| 3,485,787 | 12/1969 | Haefele | 260/33.6 |
| 3,676,387 | 7/1972 | Lindlof | 260/28.5 B |
| 3,827,999 | 8/1974 | Crossland | 260/33.6 AQ |
| 4,151,057 | 4/1979 | St. Claire et al. | 204/159.17 |
| 4,176,240 | 11/1979 | Sabia | 174/23 C |

FOREIGN PATENT DOCUMENTS

| | | |
|---|---|---|
| 1020709 | 2/1966 | United Kingdom . |
| 1035873 | 7/1966 | United Kingdom . |
| 1092563 | 11/1967 | United Kingdom . |

OTHER PUBLICATIONS

Shell Tech. Bull. SC 65-75, "Kraton G Thermoplastic Rubber for Sealants", ADH. & Related Materials, 8/1975.
SC 198-77, (8-1977), "Kraton" Shell.
"Recent Advances in Polymer Blends Grafts and Blocks", Editor L. H. Sperling Plenum Press, Poly Sci. & Tech., vol. 4, 1974, pp. 269-279.
Phillips Pet Rep 820-P-TR, "Effect of Oils on Solprrene 406".
Craver et al., Editor, "Applied Polymer Science", Organic Coatings & Plastics Chem. ACS 1975, pp. 394-429.

Primary Examiner—Melvyn I. Marquis
Assistant Examiner—Herbert J. Lilling

[57] ABSTRACT

A novel gelatinous composition is disclosed which contains an intimate melt blend admixture of poly(styrene-ethylene-butylene-styrene) triblock copolymer having said styrene end block to ethylene and butylene center block ratio within the range of from between 31:69 to 40:60, and high levels of an plasticizing oil.

The gelatinous composition is transparent and have a novel combination of properties including unexpectedly high elongation and tensile strength and excellent shape retention after extreme deformation under high-velocity impact and stress conditions. The gelatinous products of this invention are soft, flexible, and have elastic memory, characterized by a gel rigidity of from about 20 gram to about 700 gram Bloom. These and other properties are particularly essential for the gelatinous composition to have utility as toys, therapeutic hand exercising grips, shock absorbers, acoustical isolators, and other uses.

19 Claims, No Drawings

THERMOPLASTIC ELASTOMER GELATINOUS COMPOSITIONS

REFERENCE TO RELATED APPLICATION

This application is a continuation-in-part of application Ser. No. 916,731, filed June 19, 1978 and now abandoned, which is a continuation-in-part of application Ser. No. 815,315, filed July 13, 1977 and now abandoned, which is a continuation-in-part of application Ser. No. 778,343, filed Mar. 17, 1977, now abandoned.

BACKGROUND OF THE INVENTION

The present invention relates to new and particularly, useful gelatinous elastomer compositions. More specifically, the invention is directed to certain triblock copolymers modified with high levels of an plasticizing oil. The invention is further related to transparent gelatinous elastomer articles which are highly extensible and strong, extremely soft and flexible, and possess elastic memory.

It is well known that thermoplastic elastomers, more particularly, thermoplastic block copolymers can be oil-extended to produce soft and flexible compositions. However, the oil plasticized thermoplastic block copolymer compositions of the prior art suffers from one or more of the poor physical and mechanical properties such as poor breaking strength, poor elongation, poor craze, tear, creep, and crack resistance, and poor oil acceptance, to name a few. For instance, *Shell Technical Bulletin* No. SC 65-75 teaches the use of poly(styrene-ethylene-butylene-styrene) triblock copolymers having styrene end block to ethylene and butylene center block ratio of 28:72 and 29:71 in blends with butyl rubber, tackifier, filler, and oil. However, in none of the blends just described are the properties of the compositions desirable; but rather, the use of other polymers such as butyl rubber, tackifiers, and fillers for extending and plasticizing the triblock copolymers result in dimensionally unstable mastic like materials which are not acceptable for purposes of the present invention. Furthermore, when the triblock copolymers as disclosed in Shell's Bulletin No. SC 65-75 are plasticized with oil, the compositions obtained show decreases in the desired properties such as poor elongation and tensile strength, poor creep, craze, tear, and crack resistance; in addition, these compositions of the prior art tend to rupture and crumble when submitted to moderate shearing stress conditions.

SUMMARY OF THE INVENTION

Accordingly, it is an object of the present invention to provide compositions substantially free of one or more of the disadvantages of prior art compositions.

Another object is to provide gelatinous elastomer compositions which are transparent.

Yet another object is to provide gelatinous elastomer compositions of high dimensional stability, excellent crack, tear, craze, and creep resistance, improved tensile strength and high elongation.

A still further object is to provide gelatinous elastomer compositions having long service life under vibrational stress, and allows for repeated handling.

Another object is to provide gelatinous elastomer compositions having excellent processing ability for cast moulding.

Yet another object is to produce transparent, dimensionally stable, non-toxic, nearly tastless and odorless, extremely soft, highly flexible, and easily hand deformable moulded gelatinous elastomer articles prossessing elastic memory from compositions of the instant invention.

Other objects, aspects and advantages of the invention will become apparent to those skilled in the art upon consideration of the accompanying disclosure.

In accordance with the present invention, I have unexpectedly discovered that a gelatinous elastomer composition having novel combination of properties can be provided by melt blending an admixture consisting essentially of:

(A) 100 parts by weight of a triblock copolymer of the general configuration poly(styrene-ethylene-butylene-styrene) wherein said styrene end block to ethylene and butylene center block ratio is within the range of from between 31:69 to 40:60;

(B) from about 300 to about 1,600 parts by weight of an plasticizing oil selected from the group consisting of petroleum paraffinic oils, petroleum naphthenic oils, sythetic polybutene oils, synthetic polypropene oils, sythetic polyterpene oils and mixtures thereof; said oils having an average molecular weight of between about 200 to about 700.

Preferably, the triblock copolymer contemplated in (A) have a styrene end block to ethylene and butylene center block ratio of about 32:68 to about 38:62, more preferably about 32:68 to about 36:64, particularly more preferably about 32:68 to about 34:66, especially more preferably about 33:67 to about 36:64, and most preferably about 33:67. The proportion of hydrocarbon plasticizing oil contemplated in (B) is more preferably from about 350 to about 1,600 parts per 100 parts of the triblock copolymer.

DESCRIPTION OF THE PREFERRED EMBODIMENTS

The triblock copolymers employed in the present invention have the more general configuration A-B-A wherein each A is a crystalline polymer end block segment of polystyrene; and B is a elastomeric polymer center block segment of poly(ethylene-butylene). The poly(ethylene-butylene) and polystyrene portions are incompatible and form a two-phase system consisting of sub-micron domains of glassy polystyrene interconnected by flexible poly(ethylene-butylene) chains. These domains serve to crosslink and reinforce the structure. This physical elastomeric network structure is reversible, and either heating the polymer above the softening point of polystyrene temporarily disrupt the structure, which can be restored by lowering the temperature.

Plasticizers particularly preferred for use in practicing the present invention are well known in the art, they include rubber processing oils such as paraffinic and naphthenic petroleum oils, highly refined aromatic-free paraffinic and naphthenic food and technical grade white petroleum mineral oils, and synthetic liquid oligomers of polybutene, polypropene, and polyterpene. The synthetic series process oils are high molecular weight oligomers which are permanently fluid liquid monoolefins, isoparaffins or paraffins of moderate to high viscosity. Many such oils are known and commercially available.

The composition of this invention can also contain small amounts of conventionally employed additives such as stabilizers, antioxidants, antiblocking agents, colorants, fragrances, flame retardants, and the like to an extend not affecting or decreasing the desired properties of the present invention.

The triblock copolymer component by itself lacks the desired contemplated properties; whereas, when the triblock copolymer (having styrene to ethylene and butylene ratio within the range contemplated in the instant invention) is combined with selected plasticizing oils with an average molecular weight of between about 200 to about 700, as determined by ebulliscopic methods, wherein, for most purposes, the oil constitutes about 300 to about 1,600 parts and more preferably about 350 to about 1,600 parts by weight of the triblock copolymer, that an extremely soft and highly elastic material is obtained. This transformation of the triblock copolymer structure in heated oil resulting in a composition having a gel rigidity of about 20 gram to about 700 gram Bloom and substantially without oil bleedout along with high tensile strength and elongation and other desirable combination of physical properties is unexpected. As used herein, the term "gel rigidity" in gram Bloom is determined by the gram weight required to depress a gel a distance of 4 mm with a piston having a cross-sectional area of 1 square centimeter at 23° C.

The gelatinous elastomer compositions of the present invention are prepared by blending together the components including other additatives as desired at about 23° C. to about 100° C. forming a paste like mixture and further heating said mixture uniformly to about 150° C. to 200° C. until a homogeneous molten blend is obtained. These components blend easily in the melt and a heated vessel equipped with a stirrer is all that is required.

The instant composition is excellent for cast moulding and the moulded products have various excellent characteristics which cannot be anticipated from the properties of the raw components.

The basis of this invention resides in the fact that a poly(styrene-ethylene-butylene-styrene) triblock copolymer having styrene end block to ethylene and butylene center block ratio within the contemplated range of from between 31:69 to 40:60 when blended in the melt with an appropriate amount of plasticizing oil makes possible the attainment of gelatinous elastomer compositions having a desirable combination of physical and mechanical properties, notably high elongation at break of at least 1,600%, ultimate tensile strength of about at least $8 \times 10^5$ dyne/cm$^2$, low elongation set at break of substantially not greater than about 2%, tear resistance of at least $5 \times 10^5$ dyne/cm$^2$, substantially about 100% snap back when extended to 1,200% elongation, and a gel rigidity of substantially not greater than about 700 gram Bloom. More specifically, the gelatinous compositions of the present invention, as hereinbefore defined, exhibit at least seven measurable properties. They are: (1) tensile strength of about $8 \times 10^5$ dyne/cm$^2$ to about $10^7$ dyne/cm$^2$ as measured with crosshead separation speed of 25 cm per minute at 23° C.; (2) elongation of about 1,600% to about 3,000% as measured with crosshead separation speed of 25 cm per minute at 23° C.; (3) elasticity modulus of about $10^4$ dyne/cm$^2$ to about $10^6$ dyne/cm$^2$ as measured with crosshead separation speed of 25 cm per minute at 23° C.; (4) shear modulus of about $10^4$ dyne/cm$^2$ to about $10^6$ dyne/cm$^2$ as measured with a 1, 2, and 3 kilogram load at 23° C.; (5) gel rigidity of about 20 gram Bloom to about 700 gram Bloom as measured by the gram weight required to depress a gel a distance of 4 mm with a piston having a cross-sectional area of 1 square cm at 23° C.; (6) tear propagation resistance of at least $5 \times 10^5$ dyne/cm$^2$ as measured at a crosshead separation speed of 25 cm/minute at 23° C.; (7) and substantially 100% snap back recovery when extended at a crosshead separation speed of 25 cm/minute to 1,200% at 23° C.

The gelatinous elastomer articles moulded from the instant compositions have various additional important advantages in that they do not craze, creep, tear, crack, or rupture in flextural, extension, compression, or other deforming conditions of normal use; but rather the moulded articles made from the instant composition possess the intrinsic properties of elastic memory enabling the articles to recover and retain its original moulded shape after many extreme deformation cycles as compared to prior art triblock copolymer oil-extended compositions. In applications where low rigidity, high elongation, good compression set and excellent tensile strength are important, the instant compositions would be preferred.

The gelatinous elastomer compositions of the present invention are useful in low frequency vibration applications, such as viscoelastic layers in constrained-layer damping of mechanical structures and goods, as viscoelastic layers used in laminates for isolation of acoustical and mechanical noise, as viscoelastic layers used in wrappings, enclosures and linings to control sound, as compositions for use in shock and dielectric encapsulations of electrical and electronic components, as moulded shape articles for use as therapeutic hand exercising grips, as articles for use as novel amusement toys and novel re-useable lint removers.

The invention is further illustrated by means of the following illustrative embodiments, which are given for purpose of illustration only and are not meant to limit the invention to the particular reactants and amounts disclosed.

EXAMPLE I

A comparison is made between poly(styrene-ethylene-butylene-styrene) triblock copolymers having styrene end block to ethylene and butylene center block ratio below the range between 31:69 to 40:60 and ratio within the range between 31:69 to 40:60. Three different triblock copolymers were melt blended separately with a paraffinic white petroleum oil. Table I below shows the physical properties obtained with respect to each of the different styrene to ethylene and butylene ratio triblock copolymer oil-blends tested.

TABLE I

| Formulation | S/EB Ratio[1] | Weight Parts | | |
|---|---|---|---|---|
| | | A | B | C |
| S-E-B-S[2] | 28:72 | 100 | | |
| S-E-B-S[3] | 29:71 | | 100 | |
| S-E-B-S[4] | 33:67 | | | 100 |
| Paraffinic oil[5] | | 400 | 400 | 400 |
| Stabilizer[6] | | 2.5 | 2.5 | 2.5 |
| Breaking strength,[7] dyne/cm$^2$ | | $4 \times 10^5$ | $4 \times 10^5$ | $4 \times 10^6$ |
| Tear propagation,[8] dyne/cm$^2$ | | $8 \times 10^4$ | $7 \times 10^4$ | $1 \times 10^6$ |
| Elongation at break,[9] % | | 180 | 168 | 1,700 |
| Compression set[10] at 24 hours | | 81%[R] | 77%[R] | 0.0% |

TABLE I-continued

| Formulation | S/EB Ratio[1] | Weight Parts | | |
|---|---|---|---|---|
| | | A | B | C |
| Rigidity, gram Bloom | | 1,536 | 1,520 | 360 |

[1]Styrene to ethylene and butylene ratio
[2]Shell Kraton G 1650
[3]Shell Kraton G 1652
[4]Shell Kraton G 1651
[5]ARCOprime 200
[6]Irganox 1010
[7]ASTM D 412 modified
[8]ASTM D 1938 modified
[9]ASTM D 412 modified
[10]ASTM D 395 modified
[R]ruptured completely The results of Table I show drastically un-acceptable poor properties of triblock copolymers having styrene to ethylene and butylene ratios below (not within) the contemplated range of the instant invention.

EXAMPLE II

One hundred parts by weight of a poly(styrene-ethylene-butylene-styrene) triblock copolymer (Shell Kraton G 1651) having a styrene end block to ethylene and butylene center block ratio of about 33.67 with 0.1 parts by weight of a stabilizer (Irganox 1010) was melt blended with various quantities of a naphthenic oil (ARCO Tufflo 6024). Samples having the dimensions of 5 cm by 5 cm by 3 cm were cut and measured for gel rigidity on a modified Bloom gelometer as determined by the gram weight required to depress the gel a distance of 4 mm with a piston having a cross-sectional area of 1 cm$^2$. The average gel rigidity values with respect to various oil concentrations are set forth in Table II below.

TABLE II

| Oil per 100 parts of Triblock copolymer | Gel Rigidity, gram Bloom |
|---|---|
| 360 | 500 |
| 463 | 348 |
| 520 | 280 |
| 615 | 240 |
| 635 | 220 |
| 710 | 172 |
| 838 | 135 |
| 1,587 | 54 |

EXAMPLE III

Example II is repeated except about 980 parts oil is used and the gel rigidity found to be about 101 gram Bloom. Other properties measured are: tensile strength at break about $4.4 \times 10^6$ dyne/cm$^2$, elongation at break about 2,470%, elasticity modulus about $3.5 \times 10^4$ dyne/cm$^2$, and shear modulus about $3.7 \times 10^4$ dyne/cm$^2$. The tensile strength, elongation, elasticity modulus were measured with cross-head separation speed of 25 cm/minute at room temperature. The shear modulus was measured with a 1, 2, and 3 kilogram load at room temperature.

EXAMPLE IV

Example II is repeated except about 520 parts of a polybutene (Amoco Indopol H-300) is used and the gel rigidity found to be about substantially unchanged with respect to use of naphthenic oil alone.

EXAMPLE V

Example II is repeated except about 520 parts of a polypropene (Amoco C-60) is used and the gel rigidity found to be about substantially unchanged with respect to use of naphthenic oil alone.

EXAMPLE VI

Example II is repeated except about 520 parts of a polyterpene (Hercules Piccolyte S 10) is used and the gel rigidity found to be about substantially unchanged with respect to use of naphthenic oil alone.

EXAMPLE VII

Example II is repeated except about 360 parts of a combined mixture of: 72 parts of a paraffinic oil (ARCO prime 200), 72 parts of a naphthenic oil (ARCO Tufflo 6014), 72 parts of a polybutene oligomer (Amoco Indopol H-200), 72 parts of a polypropene oligomer (Amoco Polypropene C-60), and 72 parts of a polyterpene oligomer (Hercules Piccolyte S 10) is used and the gel rigidity found to be about substantially unchanged with respect to the use of naphthenic oil alone.

EXAMPLE VIII

Example III was repeated except 933 parts oil with 147 parts by weight of a poly(styrene-ethylene-butylene-styrene) triblock copolymer containing 47 parts of a naphthenic process oil (Shell Kraton G 4609) having a styrene to ethylene and butylene ratio of about 33:67 was used and the physical properties found to be about substantially unchanged with respect to the components used in Example III.

EXAMPLE IX

Example III was repeated except 933 parts oil with 147 parts by weight of a poly(styrene-ethylene-butylene-styrene) triblock copolymer containing 47 parts of a paraffinic white petroleum oil (Shell Kraton G 4609) having a styrene to ethylene and butylene block ratio of about 33:67 is used and the physical properties found to be substantially unchanged with respect to the components used in Example III.

EXAMPLE X

Example II was repeated except about 400 parts of oil was used and the properties measured were: tear propagation about $1.4 \times 10^6$ dyne/cm$^2$, no crack growth in 180° bend under 50 gram load for 5,000 hours at room temperature, tensile strength about $4 \times 10^6$ dyne/cm$^2$, elongation at break about 1,700%, tensile set about 0% at 1,200% elongation, compression set about 0% when tested under 5,000 gram load for 24 hours, and 100% snap back recovery after extension to 1,200%.

What is claimed is:

1. A gelatinous elastomer composition consisting essentially of:
   (a) 100 parts by weight of a triblock copolymer of the general configuration poly(styrene-ethylene-butylene-styrene) wherein said styrene end block to ethylene and butylene center block ratio is within the range of from between 31:69 to 40:60;
   (b) from about 300 to about 1,600 parts by weight of an plasticizing oil selected from the group consisting of petroleum paraffinic oils, petroleum naphthenic oils, synthetic polybutene oils, synthetic polypropene oils, synthetic polyterpene oils and mixtures thereof; said oils having an average molecular weight of between about 200 to about 700; and (c) said gelatinous elastomer composition being characterized as having an elongation at break of at least about 1,600%, an ultimate tensile strength of at least about $8 \times 10^5$ dyne/cm$^2$, and a gel rigidity of substantially not greater than about 700 gram Bloom.

2. A gelatinous elastomer composition as claimed in claim 1 wherein the melt blended composition exhibit at least seven measurable properties:
(a) tensil strength of about $8 \times 10^5$ dyne/cm$^2$ to about $10^7$ dyne/cm$^2$ as measured with crosshead separation speed of 25 cm per minute at 23° C.;
(b) elongation of about 1,600% to about 3,000% as measured with crosshead separation speed of 25 cm per minute at 23° C.;
(c) elasticity modulus of about $10^4$ dyne/cm$^2$ to about $10^6$ dyne/cm$^2$ as measured with crosshead separation speed of 25 cm per minute at 23° C.;
(d) shear modulus of about $10^4$ dyne/cm$^2$ to about $10^6$ dyne/cm$^2$ as measured with a 1, 2, and 3 kilogram load at 23° C.;
(e) gel rigidity of about 20 gram Bloom to about 700 gram Bloom as measured by the gram weight required to depress a gel a distance of 4 mm with a piston having a cross-sectional area of 1 square cm at 23° C.;
(f) tear propagation resistance of at least $5 \times 10^5$ dyne/cm$^2$ as measured at a crosshead separation speed of 25 cm/minute at 23° C.;
(g) and substantially 100% snap back recovery when extended at a crosshead separation speed of 25 cm/minute to 1,200% at 23° C.

3. A gelatinous elastomer composition as claimed in claim 2 wherein said styrene end block to ethylene and butylene center block ratio is about 32:68 to about 38:62.

4. A gelatinous elastomer composition as claimed in claim 2 wherein said styrene end block to ethylene and butylene center block ratio is about 32:68 to about 36.64.

5. A gelatinous elastomer composition as claimed in claim 2 wherein said styrene end block to ethylene and butylene center block ratio is about 32:68 to about 34:66.

6. A gelatinous elastomer composition as claimed in claim 2 wherein said styrene end block to ethylene and butylene center block ratio is about 33:67 to about 36:64.

7. A moulded gelatinous elastomer article wherein the article is a composition according to claim 1, 2, 3, 4, 5, or 6.

8. A gelatinous elastomer composition as claimed in claim 2 wherein said styrene end block to ethylene and butylene center block ratio is about 33:67.

9. A moulded gelatinous elastomer article wherein the article is a composition according to claim 8.

10. A gelatinous elastomer composition consisting essentially of:
(a) 100 parts by weight of a triblock copolymer of the general configuration poly(styrene-ethylene-butylene-styrene) wherein said styrene end block to ethylene and butylene center block ratio is about 32:68 to about 38:62;
(b) from about 300 to about 1,600 parts by weight of an plasticizing oil selected from the group consisting of petroleum paraffinic oils, petroleum naphthenic oils, synthetic polybutene oils, synthetic polypropene oils, synthetic polyterpene oils and mixtures thereof; said oils having an average molecular weight of between about 200 to about 700; and
(c) said gelatinous elastomer composition being characterized as having an elongation at break of at least about 1,600%, an ultimate tensile strength of at least about $8 \times 10^5$ dyne/cm$^2$, and a gel rigidity of substantially not greater than about 700 gram Bloom.

11. A moulded gelatinous elastomer article wherein the article is a composition according to claim 10.

12. A gelatinous elastomer composition consisting essentially of:
(a) 100 parts by weight of a triblock copolymer of the general configuration poly(styrene-ethylene-butylene-styrene) wherein said styrene end block to ethylene and butylene center block ratio is about 32:68 to about 36:64;
(b) from about 300 to about 1,600 parts by weight of an plasticizing oil selected from the group consisting of petroleum paraffinic oils, petroleum naphthenic oils, synthetic polybutene oils, synthetic polypropene oils, synthetic polyterpene oils and mixtures thereof; said oils having an average molecular weight of between about 200 to about 700; and
(c) said gelatinous elastomer composition being characterized as having an elongation at break of at least about 1,600%, an ultimate tensile strength of at least about $8 \times 10^5$ dyne/cm$^2$, and a gel rigidity of substantially not greater than about 700 gram Bloom.

13. A moulded gelatinous elastomer article wherein the article is a composition according to claim 12.

14. A gelatinous elastomer composition consisting essentially of:
(a) 100 parts by weight of a triblock copolymer of the general configuration poly(styrene-ethylene-butylene-styrene) wherein said styrene end block to ethylene and butylene center block ratio is about 32:68 to about 34:66;
(b) from about 300 to about 1,600 parts by weight of an plasticizing oil selected from the group consisting of petroleum paraffinic oils, petroleum naphthenic oils, synthetic polybutene oils, synthetic polypropene oils, synthetic polyterpene oils and mixtures thereof; said oils having an average molecular weight of between about 200 to about 700; and
(c) said gelatinous elastomer composition being characterized as having an elongation at break of at least about 1,600%, an ultimate tensile strength of at least about $8 \times 10^5$ dyne/cm$^2$, and a gel rigidity of substantially not greater than about 700 gram Bloom.

15. A moulded gelatinous elastomer article wherein the article is a composition according to claim 14.

16. A gelatinous elastomer composition consisting essentially of:
(A) 100 parts by weight of a triblock copolymer of the general configuration poly(styrene-ethylene-butylene-styrene) wherein said styrene end block to ethylene and butylene center block ratio is about 33:67 to about 36:64;
(B) from about 300 to about 1,600 parts by weight of an plasticizing oil selected from the group consisting of petroleum paraffinic oils, petroleum naphthenic oil, synthetic polybutene oils, synthetic polypropene oils, synthetic polyterpene oils and mixtures thereof; said oils having an average molecular weight of between about 200 to about 700.

17. A moulded gelatinous elastomer article wherein the article is a composition according to claim 16.

18. A gelatinous elastomer composition consisting essentially of:
(A) 100 parts by weight of a triblock copolymer of the general configuration poly(styrene-ethylene-butylene-styrene) wherein said styrene end block to ethylene and butylene center block ratio is about 33:67;
(B) from about 300 to about 1,600 parts by weight of an plasticizing oil selected from the group consisting of petroleum paraffinic oils, petroleum naphthenic oils, synthetic polybutene oils, synthetic polypropene oils, synthetic polyterpene oils and mixtures thereof; said oils having an average molecular weight of between about 200 to about 700.

19. A moulded gelatinous elastomer article wherein the article is a composition according to claim 18.

* * * * *